United States Patent [19]

Yamashina et al.

[11] 4,265,881

[45] May 5, 1981

[54] PLASMINOGEN-ACTIVATING SUBSTANCE AND THE PREPARATION AND USE OF SUCH SUBSTANCE

[75] Inventors: Ikuo Yamashina, Kyoto; Toshisuke Kawasaki, Hirakata; Michiko Tsukuda, Takamatsu, all of Japan

[73] Assignee: Tobishi Pharmaceutical Co., Ltd., Tokyo, Japan

[21] Appl. No.: 130,798

[22] Filed: Mar. 17, 1980

[30] Foreign Application Priority Data

Mar. 30, 1979 [JP] Japan .................................. 54-36980

[51] Int. Cl.$^3$ ............................................ A61K 35/40
[52] U.S. Cl. .................................................... 424/106
[58] Field of Search ........................................ 424/106

[56] References Cited

PUBLICATIONS

Jedrychowski et al.–Chem. Abst., vol. 88, (1978), p. 102, 366h.
Ariga–Chem. Abst., vol. 82, (1975), p. 82166p.

*Primary Examiner*—Sam Rosen
*Attorney, Agent, or Firm*—Ladas & Parry

[57] ABSTRACT

A new type of plasminogen-activating substance is extracted from the bile of hogs, which substance is characterized by;
(A) a molecular weight of 80,000 ±10,000;
(B) an isoelectric point of 7.1;
(C) an ultraviolet absorption spectrum showing a peak (λ max) at a wave length of about 278 nm;
(D) a fibrinolysis activity such that a Ca-added standard fibrin plate is lysed but a heated fibrin plate is not lysed;
(E) such a high thermal stability that heating at a temperature of 80° C. for 10 minutes causes the plasminogen-activating activity to be decreased to an extent corresponding to 50% of the original activity and heating at a temperature of 60° C. for 30 minutes causes the plasminogen-activating activity to be decreased to an extent corresponding to from 30 to 40% of the original activity;
(F) a solubility in a saline solution and an insolubility in water-soluble organic solvents, and;
(G) a synthetic substrate-lysis activity such that Glutaryl-Gly-Arg-MCA and Pro-Phe-Arg-MCA are only marginally hydrolysed.

19 Claims, 2 Drawing Figures

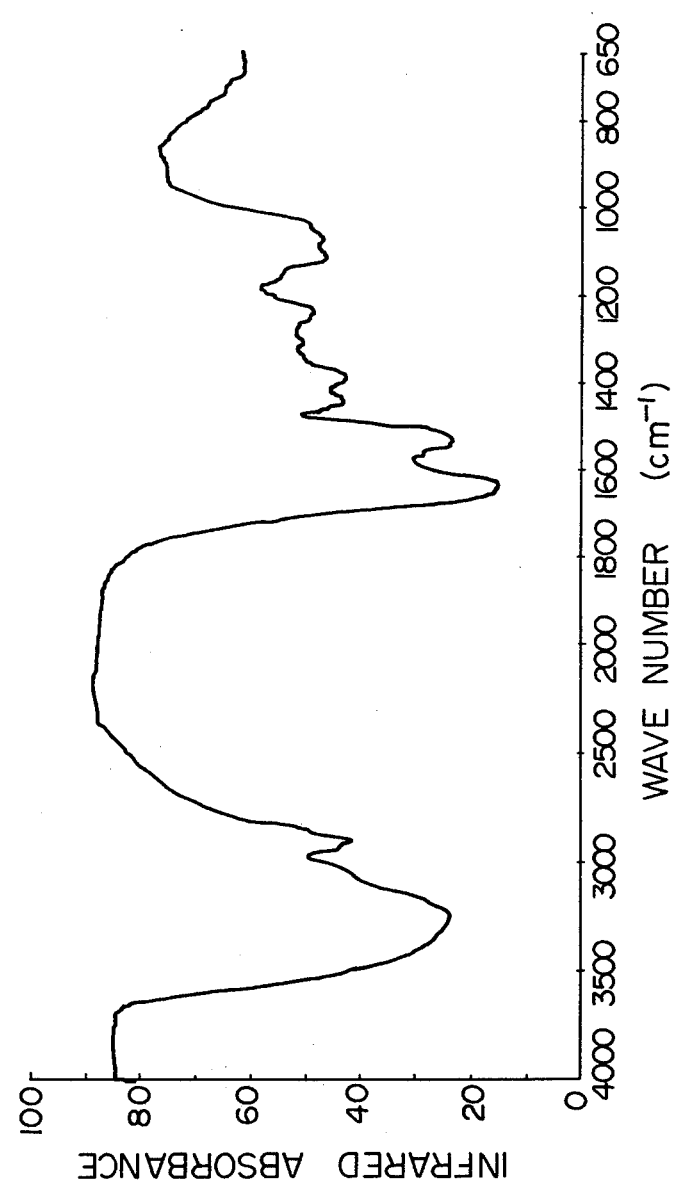

PLASMINOGEN-ACTIVATING SUBSTANCE AND THE PREPARATION AND USE OF SUCH SUBSTANCE

FIELD OF THE INVENTION

The present invention relates to a plasminogen-activating substance and the preparation and use of the substance. More particularly, the present invention relates to a plasminogen-activating substance which is an extract of the bile of hogs and exhibits an excellent plasminogen-activating activity in wide ranges of pH and temperature, and a process for preparing the substance and the use of the substance.

BACKGROUND OF THE INVENTION

It is known that the blood contains, in its normal condition, plasminogen which is not active for the fibrinolysis, and the plasminogen can be converted into plasmin, which is capable of lysing fibrin, in the presence of a plasminogen-activating substance. Such the plasminogen-activating substance is useful as a therapeutic medicine for thrombosis. At present, the plasminogen-activating substance is prepared from the urine of humans and this substance is called Urokinase. However, it is difficult to produce Urokinase on an industrial scale.

In the year 1963, it was discovered by S. Oshiba and S. Hata that the biles of dogs and rabbits contained a substance which was different from known bile acid salts but capable of activating plasminogen. Thereafter, it was revealed by them that the plasminogen-activating substance prepared from the biles of dogs and rabbits is a non-dialysable protein which belongs to a pseudo-globulin or albumin group, and can be precipitated with a 50% ammonium sulfate-saturated aqueous solution. They named their plasminogen-activating substance bilokinase (BK) [cf. J. Physiol. Soc., Japan, 29, 116–129 (1967)].

However, it was also found that the plasminogen-activating substance prepared from the biles of dogs and rabbits is easily inactivated by being heated at a temperature of 60° C. for 30 minutes and the plasminogen-activating activity thereof can be exhibited in a relatively narrow range of pH of from 4 to 9. Furthermore, it is difficult to collect the biles of dogs and rabbits in a large amount.

Under the above described circumstances, it is strongly desired to provide a new type of plasminogen-activating substance which can be easily prepared in a large amount, and exhibits an excellent plasminogen-activating activity in a wide range of pH and a high resistance to deterioration at an elevated temperature.

SUMMARY OF THE INVENTION

An object of the present invention is to provide a plasminogen-activating substance which is an extract of the bile of hogs, and which exhibits an excellent plasminogen-activating activity in a wide range of pH and a high thermal stability, a process for preparing the substance from the bile of hogs and the use of the substance as a therapeutic medicine for thrombosis.

The above-mentioned object can be attained by the plasminogen-activating substance of the present invention, which is an extract of the bile of hogs and which is characterized by:

(A) a molecular weight of 80,000±10,000;

(B) an isoelectric point of 7.1;

(C) an ultraviolet absorption spectrum showing a peak (λ max) at a wave length of about 278 nm (nonameter);

(D) a fibrinolysis activity such that a Ca-added standard fibrin plate is lysed but a heated fibrin plate is not lysed;

(E) a thermal stability such that a heating at a temperature of 80° C. for 10 minutes causes the plasminogen-activating activity to be decreased to an extent corresponding to 50% of the original activity and heating at a temperature of 60° C. for 30 minutes causes the plasminogen-activating activity to be decreased to an extent corresponding to from 30 to 40% of the original activity;

(F) a solubility in a salin solution and an insolubility in water-soluble organic solvents, and;

(G) a synthetic substrate-lysis activity such that Glutaryl-Gly-Arg-MCA and Pro-Phe-Arg-MCA are only marginally hydrolysed.

The above-specified plasminogen-activating substance can be prepared by the process of the present invention which comprises the steps of:

first fractionating the bile of hogs with a water-soluble organic solvent to prepare a first precipitate;

subjecting the first precipitate to a first extraction with a buffer solution having a pH of from 7.0 to 8.0, to prepare a first extract solution;

second fractionating the first extract solution with acetone to prepare a second precipitate;

subjecting the second precipitate to a second extraction with a buffer solution having a pH of from 7.0 to 8.0, to prepare a second extract solution, and;

third fractionating the second extract solution by a method selected from the group consisting of adsorption chromatography with hydroxylapatite, ion-exchange chromatography with an anion exchanger and hydrophobic adsorption chromatography with a hydrophobic adsorping agent to provide a fraction comprising the plasminogen-activating substance which is characterized by the above-described features.

If it is necessary, the above-described procedures may be followed by concentrating and/or additional purifying procedures for the fraction obtained by the third fractionation. Also, the plasminogen-activating substance of the present invention can be utilized as an essential component of a therapeutic medicine for thrombosis.

BRIEF DESCRIPTION OF THE DRAWINGS

In the accompanying drawings:

FIG. 2 is an infrared absorption spectrograph of the plasminogen-activating substance of the present invention.

Figure 1:
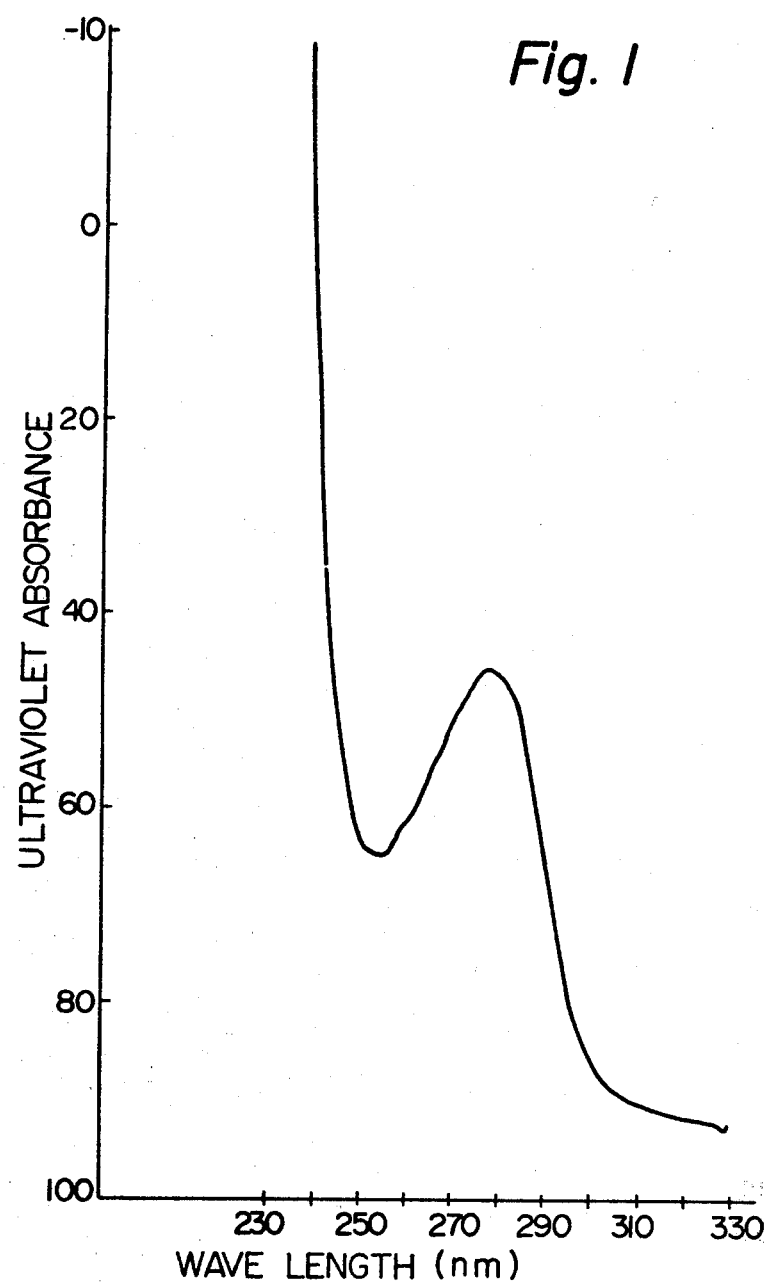
FIG. 1 is an ultraviolent adsorption spectrograph of the plasminogen-activating substance of the present invention.

The plasminogen-activating substance of the present invention is an extract of the bile of hogs and is characterized by the features as specified hereinbefore. Especially, it should be noted that the plasminogen-activating substance of the present invention exhibits not only an excellent plasminogen-activating activity in a wide range of from 3 to 10, but also, such an excellent thermal stability that heating at a temperature of 60° C. for 30 minutes results in a small decrease in the plasminogen-activating activity of from 30 to 40%.

However, the known bilokinase exhibits such a poor thermal stability that the same heating as that mentioned above causes the plasminogen-activating activity thereof to be completely inactivated. Also, the known bilokinase can exhibit the plasminogen-activating activity only in a narrow range of from 4 to 9. Accordingly, it is clear that the plasminogen-activating substance of the present invention is definitely different from the known bilokinase.

The plasminogen-activating substance of the present invention has a high molecular weight of 80,000±10,000 and exhibits a special esterase activity for hydrolysing the synthetic substrate. That is, Glutaryl-Gly-Arg-MCA and Pro-Phe-Arg-MCA are only marginally hydrolysed by the action of the plasminogen-activating substance of the present invention. However, the known urokinase which is produced from the urine of humans, can remarkably lyse Glutaryl-Gly-Arg-MCA but can not lyse Peo-Phe-Arg-MCA. Accordingly, it is evident that the plasminogen-activating substance of the present invention is definitely distinguished from Urokinase.

The inventors of the present invention named the plasminogen-activating substance of the present invention "Biloplasminokinase <Hog>". The inventors also found that the plasminogen-activating substance of the present invention is useful as an essential component of a therapeutic medicine for thrombosis, which medicine exhibits no undesirable side effect.

The plasminogen-activating substance of the present invention exhibits an ultraviolet absorption spectrum as shown in FIG. 1 of the accompanying drawing. The spectrograph shows a specific peak at a wave length of about 278 nm.

The plasminogen-activating substance of the present invention can be prepared from the bile of hogs in accordance with the above-specified process of the present invention, which comprises first fractionation, first extraction, second fractionation, second extraction and third fractionation procedures.

In the first fractionation, the bile of hogs is fractionated with a water soluble organic solvent. The water-soluble organic solvent may be selected from the group consisting of acetone, ethyl alcohol, methyl alcohol and isopropyl alcohol. The most preferable solvent is acetone.

The amount of the water-soluble organic solvent to be mixed with the bile of hogs is not limited to a specified amount. However, usually, the water soluble organic solvent is used in approximately an equivalent weight to that of the bile of hogs.

In order to promote the formation of the first precipitate, it is preferable to add a water-soluble salt to the fractionation mixture. The water-soluble salt may be selected from the group consisting of ammonium sulfate, ammonium acetate, potassium acetate and sodium acetate. Usually, the water-soluble salt is preferably used in a concentration of from 0.01 to 0.1 M.

It is also preferable that the first fractionation is carried out at room temperature or less, more preferably, 5° C. or less. For example, the bile of hogs is chilled to a temperature of about 5° C. or less and, then, mixed with the water-soluble salt in an amount sufficient to make the concentration thereof in the resultant mixture 0.01 to 0.1 M; the water-soluble organic solvent which has been chilled to a temperature of 0° C. or less, is gradually added in an equal weight to that of the bile of hogs, to the above-prepared mixture, while stirring the mixture, and; finally, the resultant mixture is left standing at a temperature of 5° C. or less, more preferably, of 0° C., so as to allow a first precipitate to be formed. The first precipitate is separated from the mixture by means of, for example, decantation and/or centrifugation.

In the first extraction, the separated precipitate is subjected to a dissolution in a buffer solution which has been controlled so as to have a pH of from 7.0 to 8.0, preferably, from 7.5 to 8.0, in order to extract soluble fractions by the buffer solution. Insoluble fraction in the first precipitate is removed from the resultant first extract solution by means of, for example, decantation, filtration and/or centrifugation.

The buffer solution for the first extraction is not limited to a special group of solutions, as long as the buffer solution exhibits a pH of from 7.0 to 8.0. Usually the buffer solution is selected from ammonium formate solutions, ammonium acetate solutions and tris-hydrochloric acid solutions, each having a pH of from 7.0 to 8.0.

The buffer solution may contain the same water-soluble salts as those used in the first fractionation, in a concentration of from 0.01 to 0.1 M. In this case, it is preferable to add urea in a concentration of from 2 to 6 M to the buffer solution. The addition of urea is effective for promoting the extraction rate of the fraction containing the essential substance of the present invention with the buffer solution. The first extraction is preferably carried out at a temperature of 5.0° C. or less.

The second fractionation is carried out by mixing acetone which has been chilled, preferably to a temperature of 0° C. or less, with the first extract solution which has been also chilled, preferably to a temperature of 5° C. or less, while stirring the mixture, to produce a second precipitate. The second fractionation may be carried out in two or more stages. For example, in a first stage of fractionation, the first extract solution is first mixed with the chilled acetone in an amount sufficient to make the concentration of the acetone in the resultant first mixture about 30% by weight, and the resultant precipitate is removed from the first mixture, and; in a second stage of fractionation, the remaining portion of the first mixture is mixed with the chilled acetone in an amount sufficient to make the concentration of the acetone in the resultant second mixture about 50% by weight, and the resultant precipitate is removed from the second mixture.

The second fractionation may be effected by mixing the first extract solution with a water-soluble calcium salt in an amount sufficient to make the concentration of the salt in the mixture 0.01 to 0.1 M. The water-soluble calcium salt may be calcium acetate and/or calcium chloride. The resulting second precipitate can be separated from the acetone-extract solution mixture by means of centrifugation.

In the second extraction, the separated second precipitate is subjected to dissolution with a buffer solution having a pH of 7.0 to 8.0, to extract a soluble fraction containing the essential substance of the present invention with the buffer solution. The insoluble fraction in the second precipitate is removed from the resultant second extract solution. Usually, the second extract solution exhibits a plasminogen-activating activity. The second extraction can be carried out in the same manner as that described for the first extraction. However, in the second extraction, it is unnecessary to add urea to the buffer solution.

The second extract solution is subjected to the third fractionation, which is carried out by a method selected from adsorption chromatography, ion-exchange chromatography and hydrophobic adsorption chromatography. Each of the above-mentioned chromatographic methods can be carried out either in a column system or a batch system.

The adsorption chromatography is carried out by using, as a fractionating agent, hydroxylapatite which has a chemical formula of $Ca_{10}(PO_4)_6(OH)_2$. When the hydroxylapatite is used, it is preferable to equilibrate it with a 0.02 M phosphate buffer solution having a pH of 7.0 and containing urea. Also, it is preferable that the urea be used in a concentration of from 2 to 6 M in the buffer solution.

When the third fractionation with the hydroxylapatite is carried out in the column system, the second extract solution is poured into a column filled with the hydroxylapatite so as to allow a fraction containing the plasminogen-activating substance of the present invention to be adsorbed by the hydroxylapatite. Next, the hydroxylapatite is washed with the same buffer solution as that used to equilibrate the hydroxylapatite, until the buffer solution which emerges from the column displays no ultraviolet absorption at a wave length of 280 nm. The fraction adsorbed by the hydroxylapatite is eluted with a 0.2 M phosphate buffer solution containing urea. The plasminogen-activating substance in the adsorbed fraction can be entirely recovered by the above-mentioned extraction.

The ion-exchange chromatography is effected by using an anion-exchanger. The anion-exchanger may be selected from cellulose derivatives having a weak basic ion-exchanging radical, for example, diethylaminoethyl cellulose; and gels, such as agarose gels and cross-linked high molecular dextron gels, for example, sephorose and diethylaminoethyl-Sephadex, which are made by Pharmacia Fine Chemicals, Sweden.

In the ion-exchange chromatographic fractionation with the anion-exchanger, a fraction containing the plasminogen-activating substance of the present invention is adsorbed by the anion-exchanger at a pH of from 5 to 8. However, in order to effect the fractionation with a high efficiency, it is preferable that the ion-exchange chromatography be carried out at a pH of from 7.5 to 8.0 by using a buffer solution containing an increased concentration of the water-soluble salt. Also, in order to enhance the solubility of the plasminogen-activating substance, it is preferable that the buffer solution contain urea in a concentration of from 2 to 6 M.

For example, the ion-exchange chromatographic fractionation can be effected in such a manner that an anion exchanger consisting of diethylaminoethyl-Sephadex A-50, which is a trademark of an anion exchanger made by Pharmacia Fine Chemicals, Sweden, is equilibrated with a 0.01 M tris-hydrochloric acid buffer solution having a pH of 8.0 and containing urea in a concentration of 2 M, and then, the second extract solution is fed into the column so as to allow a fraction containing the plasminogen-activating substance of the present invention to be adsorbed by the anion exchanger. Next, the anion exchanger in which a fraction containing the plasminogen-activating substance of the present invention is adsorbed, is washed with the same buffer solution as that used for equilibrating the anion exchanger. Finally, the fraction containing the plasminogen-activating substance is extracted with a tris-hydrochloric acid buffer solution containing sodium chloride in a concentration of 0.2 M.

The hydrophobic adsorption chromatographic fractionation is carried out by using a hydrophobic adsorping agent such as phenyl-Sepharose made by Pharmacia Fine Chemicals, Sweden. In this case, the second precipitate obtained from the second fractionation is subjected to the second extraction with a 0.05 M tris-hydrochloric acid buffer solution having a pH of 8.0. The resultant second extract solution is mixed with sodium chloride and ammonium sulfate respectively in amounts sufficient to make the concentrations thereof in the resultant mixture 1% and 10% by weight. The resultant mixture solution is fed into a column filled with the phenyl-Sepharose, so as to allow a fraction containing the plasminogen-activating substance of the present invention to be adsorbed by the phenyl-Sepharose. Thereafter, the phenyl-Sepharose is washed with the same buffer solution as that mentioned above, and a portion of the fraction containing the plasminogen-activating substance is extracted with a buffer solution which is the same as that mentioned above, except that the concentration of ammonium sulfate is reduced to 3% by weight. Finally, the remaining portion of the fraction in the column is eluted with a buffer solution which is the same as that mentioned above, except that no ammonium sulfate is contained.

The fraction recovered by the third fractionation may be concentrated and/or refined, if necessary. The concentrating procedure can be effected by a method selected from evaporation and ultrafiltration. Also, the additional purifying procedure may be effected by using a molecular sieve.

If it is necessary to refine a fraction containing the essential substance of the present invention, usually, the fraction is concentrated by means of evaporation and/or ultrafiltration, and then, subjected to the additional purification. In the additional purification, a column is charged with a molecular sieve which has been equilibrated with the same buffer solution as that used for the equilibration of the fractionating agent in the third fractionating, and then, the concentrated fraction is put on the equilibrated molecular sieve. Thereafter, a chromatographic fractionation is applied to the fraction by using the same buffer solution as that mentioned above. The above-mentioned additional purification is effective for obtaining the plasminogen-activating substance of the present invention having a high degree of purity.

The features and advantages of the present invention will be further illustrated by the examples set forth below. However, the examples are only illustrative and should in no way be interpreted as limiting the scope of the present invention.

In the examples, the plasminogen-activating activity of the substance of the present invention was represented by the fibrinolysis activity of the substance, because the fibrinolysis activity is a parameter effective for evaluating the plasminogen-activating activity. The fibrinolysis activity was determined in accordance with a fibrin plate method described by J. Ploug et al, in Biochim.Biophys, Acta., 24, 278 282 (1957). As a standard plasminogen-activating substance, urokinase having 6000 international units (IU), and made by Midori Juji Co., Japan, was used in a desired concentration (unit) thereof.

The fibrinolysis activity (A) of the plasminogen-activating substance of the present invention is determined in accordance with the equation:

$$A = B \times (a/b)$$

wherein A represents a fibrinolysis activity in units of the plasminogen-activating substance of the present invention; B represents a comparative fibrinolysis activity in units of urokinase; a represents an area of a portion of fibrin plate lysed by the plasminogen-activating substance of the present invention, and; b represents a comparative area of a portion of fibrin plate lysed by urokinase.

The esterase activity of a plasminogen-activating substance was determined by measuring the amount of 7-amino-4-methyl cumarin (MCA) which had been produced by reactions of the plasminogen-activating substance with a synthetic substrate (A) consisting of Glutaryl-Gly-Arg-MCA and with another synthetic substrate (B) consisting of Pro-Phe-Arg-MCA, at a temperature of 37° C., for 30 minutes. The measurement was effected by using a fluorophotometer and the esterase activity was represented in a unit of p mole/minutes.

The content of proteins in the plasminogen-activating substance was determined from the ultraviolet absorbance thereof at a wave length of 280 nm in accordance with the equation:

$$E_{1\%}^{2800\ nm} = 10$$

EXAMPLE 1

First fractionation

The bile of hogs in an amount of 2 liters was mixed with ammonium sulfate in an amount sufficient to cause the concentration thereof in the resultant mixture to be 10% by weight. The mixture was chilled to a temperature of 5° C. Two liters of acetone, which had been chilled to a temperature of $-10°$ C., were gradually added to the mixture while vigorously stirring the resulting admixture. The admixture was left standing at a temperature of 0° C. for a time sufficient to allow an insoluble fraction in the admixture to precipitate. The supernatant solution in the admixture was removed by means of decantation and the first precipitate was separated from the admixture and collected by means of centrifugation.

First extraction

The separated, collected first precipitate was first extracted with a 0.01 M tris-hydrochloric acid buffer solution having a pH of 8.0 and containing 5 M of urea. Insoluble substances in the first precipitate were separated from the resultant first extract solution by means of centrifugation.

Second fractionation

The first extract solution was mixed with calcium acetate in an amount sufficient to cause the concentration thereof in the resultant mixture to be 0.01 M. The mixture was cooled to a temperature of 5° C. The cooled mixture was further mixed with acetone, which had been cooled to a temperature of $-10°$ C., in an amount sufficient to cause the concentration thereof in the mixture to be 35%, so as to prepare a precipitate. The precipitate was removed from the fractionating mixture by means of centrifugation.

The remaining mixture was further mixed with the cooled acetone in an amount sufficient to cause the concentration thereof in the resulting mixture to be 50%, to form a precipitate. The precipitate was separated from the mixture by means of centrifugation and combined with the afore-mentioned obtained precipitate.

Second extraction

The precipitate was subjected to a second extraction with 500 ml of a 0.01 M tris-hydrochloric acid buffer solution, containing 2 M of urea and having a pH of 8.0. Insoluble substances in the precipitate were removed from the second extract solution. The resultant second extract solution contained 41,000 units of plasminogen-activating substance of the present invention.

Third fractionation

A column having an inner diameter of 4 cm and a height of 50 cm was filled with a fractionating agent consisting of hydroxylapatite, which had been equilibrated with a 0.02 M phosphoric acid buffer solution having a pH of 7.0 and containing 2 M of urea. The second extract solution was poured into the column, so as to allow a fraction containing the plasminogen-activating substance to be adsorbed by the hydroxylapatite. Thereafter, the fractionating agent in the column was washed with the same buffer solution as that used for equilibrating the hydroxylapatite until the buffer solution which emerged from the column displayed an ultraviolet ray absorbance of 0.05 or less at a wave length of 280 nm. In this washing operation, about 500 ml of the buffer solution were used.

Next, 300 ml of a 0.2 M phosphate buffer solution having a pH of 7.0 and containing 2 M of urea were poured into the column, to elute the adsorbed fraction containing the plasminogen-activating substance with the buffer solution. The resultant elute in a volume of about 300 ml was concentrated into a volume of 50 ml by means of ultrafiltration. The concentrated solution contained 1.2 g of the plasminogen-activating substance having a fibrinolysis activity of 30 units per mg of protein.

It was found that the resultant plasminogen-activating substance contained various amino acids, that is, Asp, Thr, Ser, Gln, Pro, Gly, Ala, Cys, Vol, Met, Ile, Lev, Tyr, Phe, Lys, His and Arg. Also, the resultant plasminogen-activating substance exhibited an infrared absortion spectrum as shown in FIG. 2.

EXAMPLE 2

The same procedures as those described in Example 1 were carried out, except that the third fractionation was carried out by the method of ion-exchange chromatography with an anion exchanger consisting of diethylaminoethyl-Sephadex A-50. In the third fractionation, an ion-exchange chromatographic column was prepared in such a manner that the diethylaminoethyl-Sephadex A-50 was impregnated and swollen with water, activated by bringing it into contact with a hydrochloric acid solution and, then, with a sodium hydroxide solution, equilibrated with a 0.01 tris-hydrochloric acid buffer solution containing urea in a concentration of 2 M, and finally, placed in a column having an inner diameter of 4 cm and a height of 50 cm.

The second extract solution in an amount of 500 ml was poured into the column, so as to allow a fraction comprising the plasminogen-activating substance to be adsorbed by the anion-exchanger. Next, the anion exchanger in the column was washed with 300 ml of the same buffer solution as that used for the equilibration, and then, 450 ml of a buffer solution which was the same as that used for equilibration, except that sodium chloride was contained therein in a concentration of 0.2 M, was poured into the column so as to elute therewith the absorbed fraction comprising the plasminogen-activating substance. After 250 ml of the buffer solution had emerged from the column, the remaining 200 ml of the buffer solution was collected. The collected solution was concentrated into a volume of 50 ml by means of ultrafiltration. The concentrated elute solution contained 1.0 g of the plasminogen-activating substance having a fibrinolysis activity of 35 units per mg of protein.

EXAMPLE 3

Additional purification with molecular sieve

A purification column was prepared in such a manner that Sephadex G-150, which is a trademark of a molecular sieve made by Pharmacia Fine Chemicals, was completely swollen with water and equilibrated with a 0.01 M ammonium formate buffer solution, and the equilibrated molecular sieve was placed in a vertical tube having an inner diameter of 4 cm and a length of 100 cm. The mixture of the concentrated fractions obtained in Examples 1 and 2 was poured into the column, so as to allow a fraction comprising the purified plasminogen-activating substance to be adsorbed by the molecular sieve. Next, 850 ml of a buffer solution which was the same as that used for the equilibration were poured into the column to elute the fraction from the molecular sieve. After 700 ml of the buffer solution had emerged from the column, the remaining 150 ml of buffer solution were collected from the column. The collected solution was freeze-dried. 680 mg of a dried plasminogen-activating substance, having a fibrinolysis activity of 50 units per mg of protein, were obtained.

The esterase activity of the resultant plasminogen-activating substance is indicated in Table 1 in comparison with that of urakinase.

TABLE 1

| Substance | Esterase activity (p mole/min) | |
| --- | --- | --- |
| | Glutaryl—Gly—Arg—MCA | Pro—Phe—Arg—MCA |
| Urokinase | 8.11 | none |
| The plasminogen-activating substance of the present invention | 0.52 | 2.66 |

Note:
Each substance was used in a concentration of 20 units of fibrinolysis activity per ml.

Table 1 clearly shows that the esterase activity of the plasminogen-activating substance of the present invention is remarkably different from that of Urokinase.

EXAMPLE 4

The same procedures as those described in Example 1 were carried out, except that phenyl-Sepharose CL-4B, which is a trademark of a hydrophobic adsorbant made by Pharmacia Fine Chemicals, Sweden, was placed, instead of the hydroxylapatite, into the column, and then, equilibrated with a 0.05 M tris-hydrochloric acid buffer solution containing urea in a concentration of 5 M. The second precipitate was subjected to the second extraction with the same buffer solution as that used for the above-mentioned equilibration. The resultant second extract solution was poured into the above-mentioned column so as to allow a fraction containing the plasminogen-activating substance to be adsorbed by phenylsepharose CL-4B. Next, the same buffer solution as that used for the equilibration was mixed with sodium chloride and ammonium sulfate respectively in amounts sufficient to cause the concentrations thereof in the resultant mixture solution to be 1% and 10%, and the mixture was poured into the column to wash it. Thereafter, the fraction in the column was eluted by pouring a mixture solution which was the same as that mentioned above, except that the concentration of ammonium sulfate was adjusted to 3%, and then, by pouring a mixture solution which was the same as that mentioned above, except that no ammonium sulfate was contained therein.

The resultant solution from the column was collected and concentrated by means of ultrafiltration. Finally, the concentrated extract was additionally purified by using the same molecular sieve as that described in Example 3. The resultant purified, extract exhibited the same fibrinolysis activity as that of Example 1.

We claim:

1. A plasminogen-activating substance which is an extract of the bile of hogs and which is characterized by:
   (A) a molecular weight of $80,000 \pm 10,000$;
   (B) an isoelectric point of 7.1;
   (C) an ultraviolet absorption spectrum showing a peak ($\lambda$ max) at a wave length of about 278 nm:
   (D) a fibrin-lysis activity such that a Ca-added standard fibrin plate is lysed but a heated fibrin plate is not lysed;
   (E) a thermal stability such that heating at a temperature of 80° C. for 10 minutes causes the plasminogen-activating activity to be decreased to an extent corresponding to 50% of the original activity and heating at a temperature of 60° C. for 30 minutes causes the plasminogen-activating activity to be decreased to an extent corresponding to from 30 to 40% of the original activity;
   (F) a solubility in a salin solution and an insolubility in water-soluble organic solvents, and;
   (G) a synthetic substrate-lysis activity such that Glutaryl-Gly-Arg-MCA and Pro-Phe-Arg-MCA are only marginally hydrolysed.

2. A process for preparing a plasminogen-activating substance from the bile of hogs, comprising the steps of:
   first fractionating the bile of hogs with a water-soluble organic solvent to prepare a first precipitate;
   subjecting said first precipitate to a first extraction with a buffer solution having a pH of from 7.0 to 8.0, to prepare a first extract solution;
   second fractionating said first extract solution with acetone to prepare a second precipitate;
   subjecting said second precipitate to a second extraction with a buffer solution having a pH of from 7.0 to 8.0 to prepare a second extract solution, and;
   third fractionating said second extract solution by a method selected from the group consisting of absorption chromatography with hydroxylapatite, ion-exchange chromatography with an anion exchanger, and hydrophobic adsorption chromatography with a hydrophobic adsorping agent, to provide a fraction comprising the plasminogen-activating substance which is characterized by:
   (A) a molecular weight of $80,000 \pm 10,000$;
   (B) an isoelectric point of 7.1;
   (C) an ultraviolet absorption spectrum showing a peak ($\lambda$ max) at a wave length of about 278 nm;

(D) a fibrin-lysis activity such that a Ca-added standard fibrin plate is lysed but a heated fibrin plate is not lysed;
(E) a thermal stability such that heating at a temperature of 80° C. for 10 minutes causes the plasminogen-activating activity to be decreased to an extent corresponding to 50% of the original activity and heating at a temperature of 60° C. for 30 minutes causes the plasminogen-activating activity to be decreased to an extent corresponding to from 30 to 40% of the original activity;
(F) a solubility in a salin solution and an insolubility in water-soluble organic solvents, and;
(G) a synthetic substrate-lysis activity such that Glutaryl-Gly-Arg-MCA and Pro-Phe-Arg-MCA are only marginally hydrolysed.

3. A process as claimed in claim 2, wherein said water-soluble organic solvent is selected from the group consisting of acetone, methyl alcohol, ethyl alcohol and isopropyl alcohol.

4. A process as claimed in claim 2, wherein said first fractionating operation is carried out in the presence of a water-soluble salt.

5. A process as claimed in claim 4, wherein said water-soluble salt is selected from the group consisting of ammonium sulfate, ammonium acetate, potassium acetate and sodium acetate.

6. A process as claimed in claim 2 wherein said first fractionating operation is carried out at room temperature or lower.

7. A process as claimed in claim 2, wherein said buffer solution for said first extraction is selected from the group consisting of ammonium formate solutions, ammonium acetate solutions, tris hydrochloric acid solutions and sodium phosphate solutions, each having a pH of from 7.0 to 8.0.

8. A process as claimed in claim 2 wherein said buffer solution for said first extraction contains ammonium sulfate in a molar concentration of from 0.01 to 0.1 M.

9. A process as claimed in claim 8, wherein said buffer solution for said first extraction contains, in addition to the ammonium sulfate, urea in a molar concentration of from 2 to 6 M.

10. A process as claimed in claim 2, wherein said first extraction is carried out at a temperature of 5° C. or less.

11. A process as claimed in claim 2, wherein said second fractionating operation is carried out at a temperature of 5° C. or less.

12. A process as claimed in claim 2, wherein said first extract solution contains a water-soluble calcium salt in a molar concentration of from 0.01 to 0.1 M.

13. A process as claimed in claim 12, wherein said water-soluble calcium salt is selected from the group consisting of calcium acetate and calcium chloride.

14. A process as claimed in claim 2, wherein said hydroxylapatite is equilibrated with a 0.02 M phosphate buffer solution having a pH of 7.0 and containing urea in a molar concentration of from 2 to 6 M.

15. A process as claimed in claim 2, wherein said anion exchanger for said ion-exchange chromatography is selected from the group consisting of cellulose derivatives having a weak basic anion-exchanging radical and gels.

16. A process as claimed in claim 2, wherein said ion-exchange chromatography is carried out at a pH of from 5 to 8.

17. A process as claimed in claim 2, wherein said fraction obtained by said third fractionation is concentrated by a method selected from the group consisting of evaporation and ultrafiltration.

18. A process as claimed in claim 2, wherein said fraction obtained by said third fractionation is additionally purified by means of a molecular sieve.

19. A therapeutic medicine for thrombosis, comprising, as an essential component thereof, a plasminogen-activating substance which is an extract of the bile of hogs and which is characterized by;
(A) a molecular weight of $80,000 \pm 10,000$;
(B) an isoelectric point of 7.1;
(C) an ultraviolet absorption spectrum showing a peak ($\lambda$ max) at a wave length of about 278 nm;
(D) a fibrin-lysis activity such that a Ca-added standard fibrin plate is lysed but a heated fibrin plate is not lysed;
(E) a thermal stability such that heating at a temperature of 80° C. for 10 minutes causes the plasminogen-activating activity to be decreased to an extent corresponding to 50% of the original activity and heating at a temperature of 60° C. for 30 minutes causes the plasminogen-activating activity to be decreased to an extent corresponding to from 30 to 40% of the original activity;
(F) a solubility in a salin solution and an insolubility in water-soluble organic solvents, and;
(G) a synthetic substrate-lysis activity such the Glutaryl-Gly-Arg-MCA and Pro-Phe-Arg-MCA are only marginally hydrolysed.

* * * * *